United States Patent
Maenz et al.

(10) Patent No.: US 6,800,308 B2
(45) Date of Patent: Oct. 5, 2004

(54) FRACTIONATION AND PROCESSING OF OILSEED MEAL

(75) Inventors: David D. Maenz, Saskatoon (CA); Rex W. Newkirk, Saskatoon (CA); Henry L. Classen, Saskatoon (CA); Robert T. Tyler, Saskatoon (CA)

(73) Assignee: University of Saskatchewan Technologies Inc., Saskatoon (CA)

( * ) Notice: Subject to any disclaimer, the term of this patent is extended or adjusted under 35 U.S.C. 154(b) by 0 days.

(21) Appl. No.: 10/275,277

(22) PCT Filed: May 14, 2001

(86) PCT No.: PCT/CA01/00693
§ 371 (c)(1),
(2), (4) Date: Jul. 23, 2003

(87) PCT Pub. No.: WO01/87083
PCT Pub. Date: Nov. 22, 2001

(65) Prior Publication Data
US 2004/0101614 A1 May 27, 2004

Related U.S. Application Data
(60) Provisional application No. 60/204,120, filed on May 15, 2000.

(51) Int. Cl.⁷ .................................................. A23G 1/02
(52) U.S. Cl. ........................... 426/44; 426/52; 426/629; 426/430
(58) Field of Search ........................... 426/44, 52, 629, 426/655, 430, 479

(56) References Cited

U.S. PATENT DOCUMENTS

| | | | |
|---|---|---|---|
| 3,736,147 A | | 5/1973 | Iacobucci et al. ............... 99/17 |
| 3,966,971 A | | 6/1976 | Morehouse et al. ........... 426/44 |
| 4,418,013 A | * | 11/1983 | Cameron et al. ............ 530/377 |
| 4,435,319 A | * | 3/1984 | Pearce ......................... 530/377 |
| 5,658,714 A | | 8/1997 | Westfall et al. .............. 530/378 |
| 6,440,479 B1 | * | 8/2002 | Myllymaki .................. 426/483 |
| 6,537,597 B1 | * | 3/2003 | Nakamori et al. ............. 426/46 |

FOREIGN PATENT DOCUMENTS

| | | | |
|---|---|---|---|
| EP | 0 925 723 | 6/1999 | ............. A23J/3/14 |
| EP | 0 976 331 | 2/2000 | ............. A23J/3/34 |
| WO | WO 98/56260 | 12/1998 | |

OTHER PUBLICATIONS

Tzeng et al. "Production of Canola Protein materials by alkaline extraction, precipitation and membrane processing". J. Food Sci. 55(4): 1147–1151, 1156. Mar. 1990.*

* cited by examiner

*Primary Examiner*—Keith Hendricks

(57) ABSTRACT

The present invention relates to a process for the aqueous extraction, fractionation and enzymatic treatment of oilseed materials to generate valued products with no significant low value by-product or waste streams. In particular, the fractionation scheme generates a protein-fiber feed ingredient principally for use with ruminant animals and a second dephytinized high protein fraction. The dephytinized high protein fraction has value as feed ingredient for a variety of species of animals.

17 Claims, 1 Drawing Sheet

FRACTIONATION AND PROCESSING OF OILSEED MEAL

CROSS-REFERENCE TO RELATED APPLICATION

This application claims the benefit of U.S. Provisional Application Ser. No. 60/204,120, filed May 15, 2000 and relates to International Application No. PCT/CA01/00693 filed May 14, 2001.

TECHNICAL FIELD

This invention generally relates to a process for the aqueous extraction, fractionation and enzymatic treatment of oilseed materials to generate valued products with no significant low value by-product or waste streams. In particular, the fractionation scheme generates a protein-fibre feed ingredient principally for use with ruminant animals and a second dephytinized high protein fraction. The dephytinized high protein fraction has value as feed ingredient for a variety of species of animals.

BACKGROUND ART

Considerable efforts have been directed toward developing aqueous processing systems and techniques for the production of high valued protein concentrates and protein isolates (>90% protein) from oilseeds such as soybean. The objective of all of these existing processing systems and techniques is to generate a single very high valued protein product. Little or no consideration is given to the value of the non-protein component of the starting material. Processing systems have not been devised to fractionate the starting material into a series of valued products without generation of low-valued by-product or waste streams.

Techniques and processing systems targeted toward production of a single high valued protein product from oilseeds often make use of high levels of water and chemicals such as salts, acid or base to achieve efficient protein extraction and isolation. Systems requiring extensive use of water and chemicals are often costly. Further costs are associated with disposing of low-value by-products or waste streams.

Canola or rapeseed consists of approximately 40% oil and 60% non-oil constituents. In commercial processing, most of the oil is removed from the seed either by solvent extraction or by expelling. In processing systems based on solvent extraction, the non-oil material initially exists as a solvent laden white flake or marc. Typically, solvent is removed from the white flake by a process that involves application of steam and heat to generate a final desolventized-toasted product called meal. The meal contains about 35% protein and is sold as a feed ingredient for inclusion in diets feed to a variety of classes of animals including swine, poultry and cattle.

Canola seed protein has excellent feeding value. The protein is rich in methionine (2.0% of total protein) and lysine (5.8% of total protein) with good balance of essential amino acids. In reviewing the nutritional quality of various protein sources, Friedman M. (J. Agric. Food Chem. 44:6–29, 1996) reported a protein efficiency ratio (PER) of 3.29 for rapeseed protein concentrate, 3.13 for casein and 1.60 for soy concentrate. Rapeseed protein concentrate had the highest PER of all of vegetable protein sources reported. As such canola or rapeseed protein, in itself, has excellent feeding value, and can be considered as exceptional in comparison to other plant proteins. Prendergast, A. F., et al. (Nort. Aquacult. 10:15–20, 1994) found that dephytinized rapeseed protein concentrate could replace 100% of the high quality fishmeal in diets feed to rainbow trout without adversely affecting growth performance and feed efficiency of the fish.

Animals do not fully utilize the protein feeding value of canola or rapeseed protein when the protein is supplied in the conventional form as part of the meal. Non-dehulled desolventized-toasted canola meal contains high levels of fibre. Fibre has little feeding for animals such as fish, chickens and young pigs and thus dilutes the protein and energy content of the meal. Further, antinutritional factors, such as phenolics, associated with the fibre may have a negative impact on the performance of monogastric animals such as pigs, chickens and fish. The toasting process employed during preparation of the final meal product decreases the protein solubility of the meal and has been shown to decrease lysine digestibility when fed to chickens (Newkirk, R. W., et al. Poult.Sci. 79:64, 2000). Canola meal contains exceptionally high levels of phytic acid (approximately 3% of the meal). Phytic acid is the storage form of phosphorus in the seed and is poorly digested by monogastric species such as pigs, chickens and fish. Phytic acid can form complexes with minerals, amino acids and proteins and thereby decrease nutrient digestibility. Further, the phosphorus in the phytic acid molecule is largely unavailable to the animal and voided with the faeces. Given this poor digestibility of phytate-P, diets must be formulated with sufficient available dietary P to meet the requirements of the animal and this often increases the cost of the ration. In addition, undigested P in the manure can be damaging to the environment and is of considerable concern in areas of intensive livestock production. Overall, the high fibre and high phytate content of canola meal limits the feeding value as a protein source for monogastric animals such as pigs, chickens and fish.

Ruminant animals, such as cattle, can extract energy from fibre through fermentation in the rumen. Further, rumen microbes can efficiently hydrolyse phytate and thus the potential for antinutritional effects and damage to the environment from dietary phytic acid is less of a concern in feeding ruminant animals. Highly soluble protein is rapidly hydrolysed and utilized by microbes in the rumen. Protein that is resistant to degradation in the rumen but is largely digested during subsequent passage through the small intestine has the highest protein feeding value for ruminant animals. As feed ingredients for ruminant animals, the highly soluble proteins in canola seed are of lower feeding value than the fraction of total canola proteins that are relatively insoluble.

Prior art in this area is focused on methods to achieve efficient protein extraction from oilseed based starting material followed by concentration or isolation of the protein into a single high valued product.

U.S. Pat. No. 5,658,714 teaches that protein can be efficiently extracted from vegetable flour by adjusting the pH of the extract media in the range from 7.0–10.0. Protein is then concentrated by ultrafiltration and precipitated by adjusting the pH of the permeate to 3.5–6.0. The phytate is resistant to the protein precipitation step and thus the phytate content of the final protein concentrate is described as less than 1% of the dry matter in the protein isolate.

U.S. Pat. No. 4,420,425 describes a process of aqueous extraction of defatted soybean using alkaline conditions with an extraction media:oilseed starting material ratio of >10:1. In this process, solids in the extract are removed by filtration, the solubilized protein is pasteurised, and the extract is passed through an ultrafiltration membrane with a molecular weight cut-off of >100,000 to generate a protein concentrate.

U.S. Pat. No. 5,989,600 teaches that the solubility of vegetable proteins can be increased by treating the vegetable protein source with enzymes such as phytase and/or proteolytic enzymes. The enzymes are directly applied to the starting material prior to any extraction phase with the objective of improving protein solubility.

U.S. Pat. No. 3,966,971 teaches that acid phytase can be added to an aqueous dispersion of vegetable protein source material to facilitate protein extraction. The aqueous slurry is maintain at a pH of minimum protein solubility for the given protein and subjected to digestion with acid phytase to promote protein solubility. The mixture is heat treated at sufficient temperature to inactivate enzyme activity and solubles are then separated from the insoluble digestion residue. Solubilized residue is described as separated from insoluble residue by centrifugation or filtration or a combination of these procedures. The pH of the liquid extract is then adjusted as desired and dried to generate a final product.

U.S. Pat. No. 4,435,319 teaches that protein can be extracted from sunflower meal by treating an aqueous slurry of the meal with an acid at a pH between 4.0 and 7.0. The soluble and insoluble residues are separated and the insoluble material in continually treated with an acid solution until the desired extraction of protein has been attained. The extracted proteins are then recovered by precipitation or by ultrafiltration.

U.S. Pat. No. 3,635,726 describes a procedure for the production of a soy protein isolate by extraction of the soy starting material under alkaline conditions whereby the pH is above the isoelectric pH of glycinin. After separating the extract from the insoluble residue the pH of the extract is reduced to the isoelectric pH of glycinin to induce protein precipitation.

U.S. Pat. No. 4,418,013 describes a process for the extraction of protein from vegetable protein sources that consists of extraction in water without the use of chemical additives in the water extraction media. The soluble extract is then separated from the solids and diluted into a body of chilled water to induce the formation of protein particles that are then removed from the water and dried to form a protein isolate of that is described as substantially undenatured.

International Patent Publication WO 95/27406 teaches that phytase can be added to water suspension of a soy-based starting material. Under controlled conditions of pH and temperature the phytate content is reduced to <50% of the phytate content in the starting material. In a preferred embodiment of this invention the starting soy material has been exposed to low heat treatment and has a nitrogen solubility index of >50%. The pH of the effluent is in the range of 7–9 and the effluent is separated into a soluble and insoluble fraction. The soluble fraction is then heat-treated to inactivate enzymes and the solubles are concentrated by nanofiltration and dried to form a final product. The insoluble fraction and the permeate formed during nanofiltration are discarded.

Tzeng et al. (Journal of Food Science 1990. 55:1147–1156) describe a series of experiments on the fractionation of various oilseed materials using an aqueous processing scheme. Commercial canola meal and oil-extracted desolventized non-toasted canola white flake were used as starting materials. All extractions were carried out under aqueous alkaline conditions of pH equal to or greater than 10. In this process, the non-extracted solids residue was separated, and the pH of the extract was adjust to 3.5 to induce isoelectric protein precipitation. The precipitated protein was separated from remaining solubles by centrifugation. The soluble protein was concentrated by ultrafiltration and diafiltration using a 10,000 molecular weight cut-off membrane. The insoluble residue, isoelectric precipitated protein and the ultrafiltered soluble protein were assayed for dry matter, protein, phytate and glucosinolate levels. Under these conditions the non-extracted residue from canola meal contained 67% of the solid and 62% of the protein present in the starting material. On a dry matter basis, the meal residue had a 42% protein and a 5.7% phytate content; the isoelectric precipitate protein had an 83% protein and a 2% phytate content; and the soluble protein had an 86% protein and a 1.7% phytate content. The isoelectric and soluble protein contained 22% and 11% respectively of the total protein in the canola meal starting material. In comparison, protein extraction under alkaline conditions was substantially higher when desolventized non-toasted canola white flake was used as a starting material. In this case, the non-extracted residue contained 50% of the solid and 15% of the protein found in the starting material. On a dry matter basis, the meal residue had an 11% protein and a 6.5% phytate content; the isoelectric precipitate protein had an 87% protein and a 1% phytate content, and the soluble protein had a 96% protein and a 1.2% phytate content. The isoelectric and soluble protein contained 43% and 33% respectively of the total protein in the canola white flake starting material. The very high nitrogen extraction from canola white flake reflects the high nitrogen solubility of the starting material in combination with alkaline extraction conditions.

DISCLOSURE OF THE INVENTION

Figure 1:
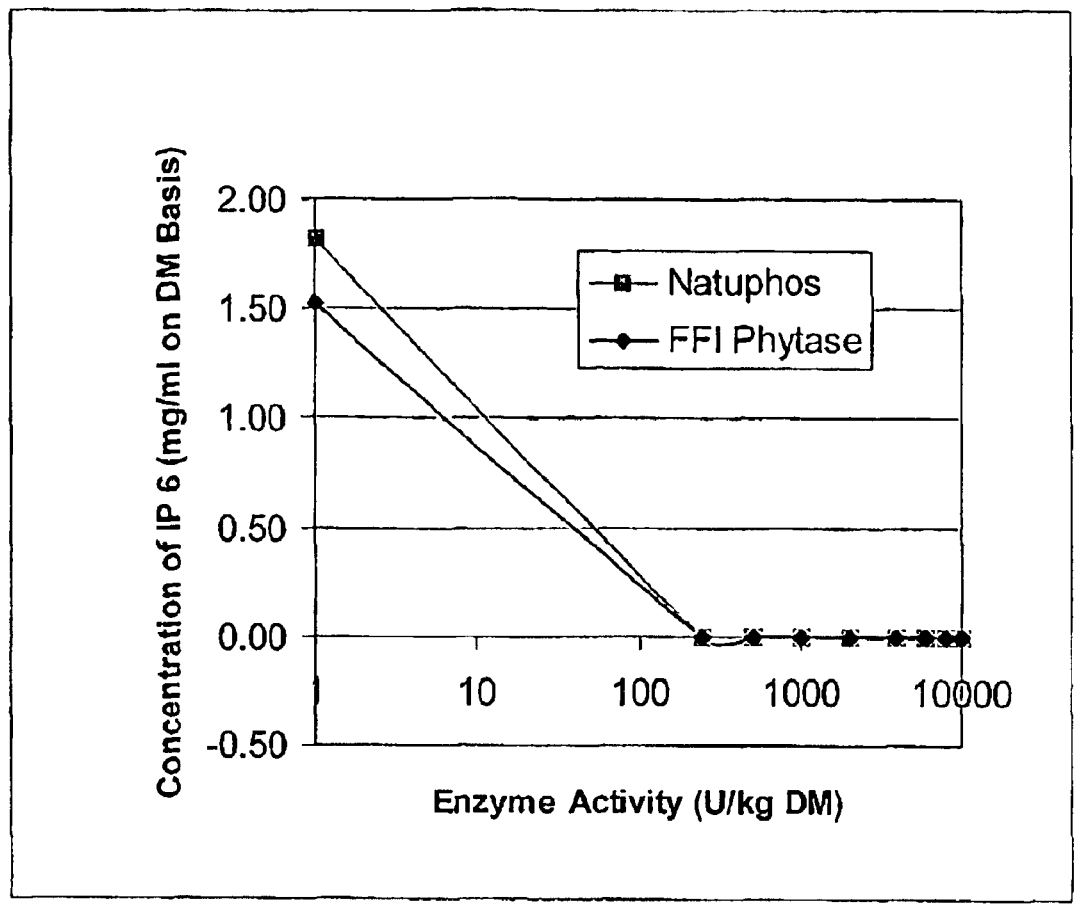
FIG. 1 illustrates the phytate concentration of a canola extract after 60 minutes of hydrolysis with either FFI or Natuphos phytases.

The present invention in its broadest aspect relates to a process for the aqueous extraction and fractionation of an oilseed starting material, such as oil-extracted desolventized flakes originating from rapeseed or canola. This oilseed material is first solvent extracted using an aqueous solvent and an aqueous extract is separated from the remaining solids. The aqueous extract is dephytinized by treatment with a phytase enriched enzyme.

The dephytinized extract thus obtained may be heat treated to induce curdling of protein contained in the extract. This precipitated protein can then be separated from the remaining liquid by a solid-liquid separation.

The result is a series of valuable products without the generation of by-product or waste streams. The process of the invention provides an efficient extraction while maintaining a protein content in the non-extracted material such that it has a good feeding value as a protein-fibre for ruminant animals. The liquid extract obtained after separation of the precipitated protein may be further processed by membrane filtration and subsequent generation of high value products.

BEST MODES FOR CARRYING OUT THE INVENTION

Full utilization of the inherent value of the non-oil constituents of an oilseed, such as rapeseed or canola, requires a fractionation process wherein the constituent are partitioned into distinct products with good value for targeted uses. A fractionation-processing system according to the present invention satisfies the following criteria:

All of the products have good value, for example for feed ingredients for a variety of species such as fish, pigs, chickens and cattle, or food ingredients for human use.

The efficiency of extraction of nutrients such as protein is adequate to generate substantial quantities of high valued products but must not overly compromise the value of the extracted residue. The extracted residue retains good value as a protein-fibre for ruminant animals. The content of fibre and antiniatritional factors, such as phytic acid, in high valued products is zero or at tolerably low levels. The process does not generate low valued by-product or waste streams.

The fractionation processing system generates dewatered intermediate products with minimal moisture content to decrease the drying costs of the overall process.

The fractionation-processing system does not require excess moisture or chemicals that increase the overall costs of the process either through loss and replacement or through the costs associated with recycling the moisture and chemicals.

Accordingly, the present invention discloses a fractionation-processing scheme that can be used with an oilseed material, such as canola or rapeseed, to effectively fractionate the non-oil components of the oilseed into distinct products. Each of these products has considerable value and thus the process does not generate any substantive waste or by-product streams. Further, the process generates dewatered intermediate products with minimal moisture content and does not require high levels of moisture or chemicals. The process is distinct from prior art that is focused on highly efficient extraction and isolation of protein from oilseeds and not upon effective fractionation of the material into high valued products that make full use of the non-oil components of the seed.

The invention uses oilseed materials originating from rapeseed or canola, as a starting material. Particularly, the starting material is oil-extracted non- or lightly toasted flakes from rapeseed or cranola. In the present invention, non- or lightly toasted flakes are defined as the residue of the seed that remains after oil-extraction, wherein this material has been desolventized without exposure to substantial heat. More precisely, non- or lightly toasted flakes are defined as having a nitrogen dispersibility index (NFI) of >50%. Nitrogen dispersibility index can be determined by AOCS official method Ba.

The present invention describes a 2-step extraction and dephytinization process. In the first step, the staring material is mixed with an aqueous extraction media preferably at 10% (w/v) to 50% (w/v), more preferably at 15% (w/v) to about 30% (w/v). The aqueous extraction media may contain salt, such as NaCl or KCl; acid, such as HCl or citric acid; or base, such as NaOH or KOH., Salts can be present at <2% (w/v). Acids can be included such that the pH of the extraction media is >2, and bases can be included such that the pH<12. In a preferred embodiment of the invention the extraction media consists of water with no addition of salt, acid or base.

After mixing of the starting material with the extraction media, the mixture is dewatered using systems such as compression and/or vacuum filtration and screen sieving or any other separation system that will remove an extract consisting of liquid containing soluble materials plus small solid fragments. The small solid fragments in the extract are primarily comprised of cell meats. The extracted residue material consists of larger extracted particles such as hulls and larger fragments of extracted cell meats. Most of the phenolic compounds in the starting material are found in the fibre structures in the seed hulls. Under the mild extraction conditions with no use of acid, base or salt in the extraction media employed un this invention, oxidation of phenolics does not occur and inclusion of high levels of compounds such as $Na_2SO_3$ that inhibit oxidation of phenolics is not required.

Removal of small fragments of cell meats along with solubles in the bulk extract results in an efficient yet balanced extraction. More than 30%, preferably more than 50% of the total protein is recovered in the bulk extract. In a preferred aspect of the invention approximately 65% of the total protein is recovered in the bulk extract. According to the invention, the extracted material retains considerably value as a protein-fibre feed for ruminant animals. The protein content is >20%, preferably >30% of the dry matter in the extracted material. Dewatering of the extracted material is a relatively efficient process such that the moisture content after the dewatering process is <70% of the total mass. In the present invention, the option exits to further process the dewatered extracted material to increase the value of this material as a protein-fibre feed ingredient. For example, the material could be further treated with a chemical such as NaOH, in the known way, to increase fibre digestibility. In addition, known methods of physical fibre disruption such as steam or ammonia-based fibre explosion could be used to increase fibre digestibility. Finally, the material could be treated with fibre-degrading enzymes such as ferulic acid esterase, cellulose and hemicellulase to increase the digestibility of the fibre within the product when fed to ruminant animals. According to the invention, the dewatered extracted material can be dried, in the known way, to produce a final product with good value as a protein-fibre feed for ruminant animals such as cattle and sheep.

In the second step the invention, the extract is wholly or partially dephytinized by incubation with a phytase-enriched enzyme product under controlled conditions of temperature and duration. The pH of the bulk extract can be modified to promote enzyme activity. Further, chemical chelators, such as citric acid can be added to the extract to promote the dephytinization process. Maenz, D. D., et al. (Ani. Feed Sci. Tech. 81:177–192, 1999) demonstrated that chelators such as citric acid when added to an aqueous slurry of phytase containing canola meal will enhance the dephytinization process. Presumably this occurs through a mechanism of competitive chelation whereby the chelator binds minerals thereby decreasing mineral binding to phytic acid and increasing the susceptibility of the substrate to hydrolysis by the enzyme. In a preferred embodiment of the invention, no pH modification and no chemical chelators are used in the dephytinization step. According to the invention, enzyme incubation can occur from 1–600 minutes at a temperature of 10–70° C. However, the process of dephytinizaiton is relatively efficient, and, in a preferred embodiment of the invention the reaction occurs for 60 minutes at 50° C. More than 50%, preferably more than 70%, of the total phytate in the bulk extract is hydrolysed during the enzyme treatment phase.

In the present invention, the protein content of the dephytinized extract is >40%, preferably >50% of the dry matter. The phytate content of the dephytinized extract is <1.0%, preferably <0.5%, of the dry matter. The option exists to dry the extract, in the known way, to generate a low phytate, high protein product. This product would have good value as a feed ingredient for animals such as fish, swine, poultry, ruminant and companion animals.

In a preferred embodiment to the invention, the value of the extract is increased by further fractionation. As an example, a portion of the protein in the extract can be precipitated, in the known way, by techniques such as isoelectric precipitation. In this particular method the pH of the extract is adjust to the pKa value of proteins in solution in the extract to induce precipitation. Precipitated proteins are then separated from the liquid and dried to form a low phytate, high protein product. In a second example, proteins in the extract can be concentrated, in the known way, by techniques such as membrane filtration, that separate molecules in solution based on differences in molecular weight. By passing the extract through an ultrafiltration membrane, soluble proteins are concentrated in the retentate and partially separated from lower molecular weight compounds. The protein concentrate formed during this ultrafiltration step can be dried to generate a low phytate, high protein product. Further, two or more protein concentration steps can be carried out in sequence to produce multiple products from the extract. As an example, a precipitation step, such as isoelectric precipitation, can be used to precipitate a portion of the total protein in the extract. This material can be removed from the liquid and the liquid can then be passed through an ultrafiltration membrane to generate a protein concentrate. In this system two protein products are prepared from the extract.

In a preferred embodiment to the invention, the dephytinized extract is further processed by heat-treatment. The dephytinized extract is heated at >80° C. for more than 1 min. In a preferred embodiment, the temperature of the dephytinized extract is increased to 95° C. and maintained for 5 minutes. A portion of the total protein in the extract is susceptible to heat-induced protein curdling. Further, the heat-treatment process serves to pasteurise the extract and thereby reduce the bacterial load in the final products. In addition, heat-treatment will denature any enzyme activity added to the extract during the enzyme-treatment phase. Optionally, chemicals such as $CaSO_4$ that are known to enhance heat-induced protein curdling are added to the extract. In addition, an acid such as HCl or a base such as NaOH, are optionally added to the extract to enhance the process of heat-induced curdling. In a preferred embodiment, no chemicals are added and heat-induced protein curdling occurs without supplementation of the extract. The heat-treated dephytinized extract is then processed by systems such as sieving through metal screens in combination with compression and/or vacuum filtration and/or any other separation systems that effectively removes the liquid from the solids (curdled protein plus small solid fragments). According to the invention, >30%, preferably >50%, of the total protein in the heat-treated dephytinized extract is in the form of solids that can be readily dewatered as described above. Dewatering is an efficient process such that the moisture content after the dewatering process is <70% of the total mass of the dewatered solids. The low moisture content of a dewatered protein product formed from an extract is unexpected and useful in that substantial savings will occur via lower drying costs to generate the final product. According to the invention, protein accounts for >45%, preferably >55%, of the dry matter in the dewatered solids that are separated from the heat-treated, dephytinized extract. According to the invention, the phytate content is <1%, preferably <0.5%, of the dry matter in the dewatered solids. In the present invention, the dewatered solids can be readily dried, in the known way, to produce a low phytate, high protein product with excellent feeding value for a variety of species of animals including fish, swine, poultry, ruminant and companion animals.

The liquid phase formed during the dewatering of the heat-treated, dephytinized extract will contain, primarily, soluble carbohydrates and soluble proteins that are resistant to heat-induced precipitation. This liquid can be dried, in the known way, to generate an energy-protein product that would have value as a feed ingredient for a variety of species of animals including fish, swine, poultry, ruminant and companion animals.

In a preferred embodiment of the invention, the liquid phase formed during dewatering of the heat-treated, dephytinized extract is further fractionated to increase the value of the material. As an example a portion of the total protein in the extract can be precipitated, in the known way, by techniques such as isoelectric precipitation. Precipitated proteins can then be separated and dried to form a low phytate high protein product. The liquid remaining after removal of the precipitated protein would contain, primarily, soluble carbohydrates and proteins that are resistant to heat-induced and isoelectric precipitation. This material could be dried to generate a product with good feeding value for animals such as swine and poultry.

In an other preferred embodiment of the invention, the liquid formed during dewatering of the heat-treated, dephytinized extract is directly processed through membrane filtration systems to separate and concentrate the constituent soluble protein and carbohydrates. Specifically, a protein concentrate with a protein content of >65%, preferably >75%, of the dry matter can be formed by passing the liquid through an ultrafiltration membrane. The protein concentrate formed during ultrafiltration can be dried, in the known way, to generate a high valued protein product. According to the invention, the phytate content of this protein concentrate is <0.1% of the dry matter. In a preferred aspect of the invention, the phytate content of the protein concentrate is not detectable. The 0-phytate, high protein concentrate has excellent value as a feed ingredient for fish, pigs, chickens and cattle. This protein concentrate has further potential for human use and consumption as a food ingredient.

Yet, in an other preferred embodiment to the invention, the permeate formed during the ultrafiltration step can be further processed by nanofiltration, to generate a carbohydrate enriched concentrate. This carbohydrate concentrate can be used directly as a liquid concentrate energy feed for animals. Alternatively, the concentrate can be dried, in the know way, and used as a dry feed ingredient. Finally, the option exists to use the liquid concentrate directly as a feedstock into a fermentation process for ethanol production.

Further, in another preferred embodiment to the invention, the permeate formed during nanofiltration can be recycled directly into the initial extraction media. The option exists to purify the water in the filtrate through reverse osmosis and thereby generate a mineral concentrate as an additional product.

The invention will be described in more detail by means of the following example. The example is provided only in order to illustrate the invention and it should not be construed to restrict the scope of the invention in any way.

EXAMPLE 1

Fractionation of Non-Toasted Canola Flakes

Hexane-laden oil-extracted canola flakes were obtained from a commercial crushing facility. This material had not undergone desolventization or toasting. The flakes were stored in burlap bags and maintained in an open-air environment for a minimum of 7 days to allow hexane to evaporate. The desolventized flakes were crumbled to break up larger masses in the flakes.

20 kg of desolventized canola flakes were mixed 60 liters of water at 50° C. in a ribbon blender for a 10-minute period. The mixture was passed through a compression belt filter press (Frontier Technologies Incorporated). The belt consisted of a 30 cm 350 CFM belt, with 9 pressure rolls and nip roll. Passage through the belt press separated the mixture into an extract and a presscake. The extract was passed through a small-scale commercial depulper fitted with a custom-built 0.15 mm opening metal screen. The depulper removed larger particles from the extract. The pulp was passed through the depulper a second to improve separation of larger particles. The pulp remaining after the second passage was mixed with the presscake material. 20 liters of water at 50° C. was added to presscake and mixed in a ribbon blender until an even consistency was obtained. The mixture was then passed through the belt filter press. The extract from this second passage through the belt press was processed through the depulper as described for the first extract. The pulp remaining from the processing the second extract was mixed into the second presscake. 10 liters of water at 50° C. was mixed with the second presscake in a ribbon mixer until an even consistency was obtained. The mixture was then processed through a 6 inch dewatering screw press (Model CP-6) Vincent Corporation to generate a extract and a presscake. The extract was processed through the depulper as previously described and the pulp was added to presscake obtained from the first passage through the screw press. 5 liters of water at 50° C. was mixed with the presscake in a ribbon mixer until an even consistency was obtained. The mixture was passed through the screw press. The extract was processed through the depulper as previously described and the pulp added to the presscake. The mixture of the pulp and presscake (without further water addition) was processed by a final passage through the screw press to generate the final presscake and an extract. All of the depulped extracts from the various steps in extraction-dewatering process were pooled and mixed to generate the final extract. The crude protein and dry matter content of the starting material, the final extract and final presscake were assayed. The protein and dry matter mass flows are shown in table 1.

TABLE 1

Protein and dry matter content and mass flows during extraction-dewatering of canola flakes.

|  | % crude protein[1] | % dry matter | % of total crude protein | % of total dry matter |
| --- | --- | --- | --- | --- |
| Canola Flakes | 39.6 | 90.9 |  |  |
| Extract | 49.3 | 13.4 | 64.3 | 51.7 |
| Presscake | 32.8 | 30.0 | 32.7 | 39.1 |

[1]Crude protein content expressed as % of dry matter
[2]Protein and dry matter content of extract and presscake expressed as a percentage of the protein and dry matter in the canola flakes starting material.

EXAMPLE 2

Dephytinization of an Extract of Canola Flakes

Phytase (Natuphos® 5000, BASF) or FFI phytase (non-commercial enzyme supplied by FinnFeeds International) was diluted in water such that a 250 µl aliquot was the equivalent of adding 0, 250, 500, 1000, 2000, 4000, 6000, 8000 and 10000 U of phytase respectively. One unit of phytase activity is defined as the amount of enzyme source that liberates 1 micromole of inorganic phosphorus per minute from an excess solution of sodium phytate at 37° C. and pH 5.5.

In a conical centrifuge tube, 20 g of non-toasted desolventized canola flakes were mixed with 100 ml of 50° C. 0.75% NaCl. The slurry was centrifuged at 3000*g for 10 minutes. The supernatant was removed and divided into 2 ml aliquots in glass test tubes and placed in a water bath at 50° C. After 60 minutes had elapsed, the reaction was stopped by adding 1 ml of ice cold 1M HCl and vortexed. The samples were left on ice to be sure the reaction had stopped. The samples were analyzed for soluble phosphorus and the 60 minute sample was analyzed for phytate.

The level of phytate in the saline extract after treating with FFI and Natuphos phytase for 60 minutes is shown in FIG. 1. Only 250 units of either phytase were required for complete dephytinization of a canola extract at pH 5.8. Earlier research showed that complete dephytinization of a canola meal slurry requires 5000 U/kg of phytase. Previous work also showed that the efficacy of dephytinization was improved by reducing the pH of a slurry to 5.0 from 5.8 but in this study, even at pH 5.8 the reaction occurred very quickly.

EXAMPLE 3

Heat-Induced Protein Curdling of a Dephytinized Extract of Canola Flakes

Non-toasted desolventized canola flakes were processed by extraction-dewatering as described in examples. In this case however, the desolventized flakes were sieved through a number 10 U.S. mesh screen to remove large aggregates from the starting material.

The final extract was placed in 100 L steam kettle and the temperature of the extract increased to 50° C. Phytase (FFI phytase as described in example 2) was added to the mixture to provide1500 FTU/kg original flake starting material. The mixture was stirred continuously with a mechanical agitator and the temperature was maintained for 60 minutes to affect dephytinzation of the extract. At the conclusion of the dephytinization period the temperature of the mixture was increased to 95° C. and this temperature was maintained for 5 minutes. At the conclusion of the heat treatment period the steam to the kettle was turned off and cold water was run through the lines. A protein-enriched curd formed on the top of the liquid and the curd hardened during a 20 minute cool down period. The entire contents of the kettle were poured through a 220 micron opening nitex screen. Solids were trapped on the screen, and the screen and contents were folded and place into a cheese mold. The protein-enriched curd was compressed at 5 PSI under a hydraulic cheese press for 10 minutes. The pressure was increased to 10 PSI and maintained for 10 minutes. The pressure was increased again to 20 PSI and maintained for another 10 minutes. The pressure was increased again to 30 PSI and maintained for another 10 minutes. Finally the pressure was increased to 40 minutes and maintained for 20 minutes. The starting flakes, final presscake, extract, dewatered protein-enriched curd, and the liquid fraction from dewatering the dephytinized heat-treated extract were assayed for protein and dry matter. The protein and dry matter content of the various fractions and the mass flows protein and dry matter is shown in table 2.

TABLE 2

Protein and dry matter content and mass flows during a process of extraction-dewatering, followed by heat-treatment and dewatering of an extract of canola flakes.

|  | % crude protein[1] | % dry matter | % of total crude protein | % of total dry matter |
| --- | --- | --- | --- | --- |
| Canola Flakes | 40.7 | 91.4 |  |  |
| Extract | 49.2 | 11.8 | 58.0 | 48.0 |
| Presscake | 33.1 | 28.3 | 31.8 | 39.1 |
| Dewatered curd | 62.1 | 29.5 | 41.9 | 27.4 |
| Liquid from dewatering of curd | 35.7 | 7.0 | 16.4 | 18.6 |

[1]Crude protein content expressed as % of dry matter
[2]Protein and dry matter content expressed as a percentage of the protein and dry matter in the canola flakes starting material.

EXAMPLE 4

Ultrafiltration of a Liquid Extract Obtained During the Dewatering of a Protein Curd Formed by Heat-Treatment of a Canola Extract.

A liquid extract was obtained by compression dewatering of protein curd that had been formed by heat-treatment of canola flake extract. The procedures for obtaining the liquid extract were the same as described in examples 1 and 3.

7.5 liters of liquid was maintained at a constant 45° C. during the filtration process. The liquid was passed through an 1812 ultrafiltration membrane with a nominal molecular weight cut-off of 10,000. The permeate was collected and the retentate concentrated to 1.5 L. After completion of the ultrafiltration a total of 6 rounds of diafiltration were run. For each run, 1.5 L of water at 45° C. was added to the retentate and the retentate filtered down to a volume of 1.5 L. The final retentate was assayed for protein and dry matter content. A final protein concentration of 91.3% (expressed as percentage of dry matter) was obtained for the retentate.

What is claimed is:

1. A process for the aqueous extraction and fractionation of an oilseed starting materials to generate valued products with no significant low value by-products or waste streams which comprises:
   (a) mixing a rapeseed or canola starting material with an aqueous solution under mild extraction conditions to form an aqueous mixture comprising an aqueous extract containing extracted protein, small solid fragments of cell meat front the rapeseed or canola and fibrous material,
   (b) subjecting said aqueous mixture to separation by means of filtration and screening to obtain a filtrate comprising an aqueous extract containing extracted protein and small solid fragments of cell meat, while leaving an extraction solids residue containing at least 20% by weight of protein based on the dry matter of the solids residue,
   (c) treating the aqueous extract and small solid fragments of cell meat with a phytase enriched enzyme to obtain a dephytinized high protein fraction containing more than 30% by weight of the total protein contained in the starting materials,
   (d) treating said dephytinized protein-enriched extract fraction to induce curdling of protein contained in said extract, and
   (e) subjecting said extract fraction containing curdled protein to solid-liquid separation so obtain a dephytinized liquid fraction containing soluble proteins and a protein-enriched dephytinized solids fraction.

2. A process according to claim 1 wherein the starting material comprises oil-extracted desolventized flakes originating from rapeseed or canola.

3. A process according to claim 2 wherein the desolventized flakes are lightly toasted flakes.

4. A process according to claim 1 wherein the dephytinized protein-enriched aqueous extract is heated to induce curdling of protein contained in the extract.

5. The process according to claim 1 wherein the oilseed starting material is mixed with the aqueous solution at a concentration of about 10 to 50% (w/v).

6. The process according to claim 1 wherein more than 50% of the total protein contained in the oilseed starting material is extracted in the filtrate.

7. The process according to claim 1 wherein the treatment with a phytase enriched enzyme is at a temperature in the range of 10 to 70° C.

8. The process according to claim 7 wherein the treatment with a phytase enriched enzyme hydrolyses more than 50% of the total phytate contained in the aqueous extract and small solid fragments of cell meat.

9. The process according to claim 8 wherein the treatment with phytase enriched enzyme is at a temperature of at least 80° C. for at least 1 minute to induce curdling of the protein.

10. The process according to claim 1 wherein the separated protein-enriched dephytinized solids fraction contain less than 1% by weight of phytate.

11. The process according to claim 1 wherein the protein-enriched dephytinized liquid fraction containing soluble proteins is further processed by ultrafiltration to concentrate and partially separate the soluble protein from lower molecular weight constituents.

12. The process according to claim 10 wherein the protein-enriched dephytinized solids fraction is dried to produce a high protein, low phytate protein concentrate.

13. A process according to claim 1 wherein the aqueous solution is water containing substantially no acid, base or salt.

14. A process according to claim 1 wherein the small solid fragments of cell meat pass through 0.15 mm screen openings.

15. A process according to claim 1 wherein said extraction solids residue from step (b) is recovered as a useful protein-fibre product.

16. A process according to claim 1 wherein said protein-enriched dephytinized solids fraction and said dephytinized liquid fraction containing soluble protein from step (e) are separately recovered as useful protein products.

17. The process according to claim 14 wherein said protein-enriched dephytinized solids fraction contains at least 45% by weight of protein based on the dry matter of the solids fraction.

* * * * *